United States Patent
Hauger et al.

[11] Patent Number: 5,832,550
[45] Date of Patent: Nov. 10, 1998

[54] MOLDABLE VACUUM CUSHION

[75] Inventors: Todd M. Hauger; Loren G. Kamstra; Vincent S. Hursh, all of Orange City, Iowa

[73] Assignee: Biotek, Orange City, Iowa

[21] Appl. No.: 909,279

[22] Filed: Aug. 11, 1997

[51] Int. Cl.[6] ................................................. A61G 15/12
[52] U.S. Cl. .................... 5/621; 5/411; 5/622; 5/640; 5/644
[58] Field of Search ........................... 5/621, 622, 640, 5/643, 644, 411, 652, 655.4, 657, 911, 912, 913

[56] References Cited

U.S. PATENT DOCUMENTS

| | | | |
|---|---|---|---|
| 2,059,875 | 11/1936 | Katz | 5/411 X |
| 2,995,762 | 8/1961 | Albinson | 5/411 |
| 4,074,373 | 2/1978 | Garofolo | 5/411 X |
| 4,346,298 | 8/1982 | Dixit | 5/644 |
| 4,493,877 | 1/1985 | Burnett | 5/913 X |
| 5,287,576 | 2/1994 | Fraser | 5/911 X |
| 5,556,169 | 9/1996 | Parrich et al. | 5/655.4 X |

FOREIGN PATENT DOCUMENTS 2214071  8/1989  United Kingdom ............... 5/655.4

*Primary Examiner*—Michael F. Trettel
*Attorney, Agent, or Firm*—Zarley, McKee, Thomte, Voorhees & Sease

[57] ABSTRACT

A moldable vacuum cushion for positioning a patient during radiation therapy treatment includes an indexing bar with indexing pins to allow the attached cushion to be quickly, easily, accurately, and repeatably indexed on a baseplate or treatment table. The indexing bar may be releasably mounted on a frame member fixed to the cushion or may be directly mounted on the cushion.

19 Claims, 5 Drawing Sheets

MOLDABLE VACUUM CUSHION

BACKGROUND OF THE INVENTION

Patient positioning systems are used for accurate and reproducible positioning of a patient for radiation therapy, diagnostic imaging, surgery, and other medical procedures. Typically, such positioning systems use a moldable cushion for patient comfort. Cushions of various shapes are used for different anatomical areas. Generally, the cushion is made of a flexible casing, such as urethane film 0.008–0.010 inch thick, containing a yieldable substance, such as a polystyrene spheres approximately 0.060 inch in diameter.

In forming the molded cushion, the cushion is initially inflated, and the patient is placed upon the soft cushion. A valve on the cushion is then connected to a vacuum compressor, which pulls a partial vacuum on the cushion until it is easily moldable. The cushion is molded to the patient's contours, creating a mold that will hold the body area in the desired position. A complete vacuum is then drawn so that the cushion becomes a rigid mold that will hold its shape for repeatable and accurate radiation treatments of a particular patient.

After the treatment sessions are completed, the molded cushion can be cleaned and reinflated for use with the next patient. Accurate positioning of the patient is critical in repeated radiation treatments, so as to ensure that radiation exposure is directed to the targeted tissue and so as to ensure that exposure of healthy tissue is minimized. Thus, it is desirable to index the molded cushion to the treatment table or to a baseplate. In conventional cushion molding processes, the cushion is molded around protrusions on the treatment table or baseplate, such that the cushion has corresponding detents. While such detent indexing works reasonably well in many instances, it does not allow or maintain close repositioning tolerances, which are needed for high precision radiation therapy treatments.

Accordingly, a primary objective of the present invention is the provision of an improved moldable cushion for accurate and reproducible patient positioning during radiation therapy treatments, diagnostic imaging and other medical procedures.

Another objective of the present invention is the provision of an improved patient positioning cushion having a frame for quick and easy use.

A further objective of the present invention is the provision of an improved indexing means for radiation therapy molded vacuum cushions.

These and other objectives will become apparent from the following description of the invention.

SUMMARY OF THE INVENTION

An improved vacuum cushion is provided for accurate and repeatable positioning of a patient on a support surface for radiation therapy treatment. The cushion includes an outer casing with a valve that is connectable to a vacuum source. The casing contains small beads. A frame member is fixed on the outer casing, and an indexing bar is connected to the frame member. In an alternative embodiment, the indexing bar is directly connected to the cushion, without a frame member. The opposite ends of the indexing bar may extend beyond the outer edges of the cushion. The bar is adapted to be secured to a baseplate or treatment table for quick and easy indexing of the cushion, and for holding the cushion in position for the treatment procedure.

DETAILED DESCRIPTION OF THE DRAWINGS

Figure 1:
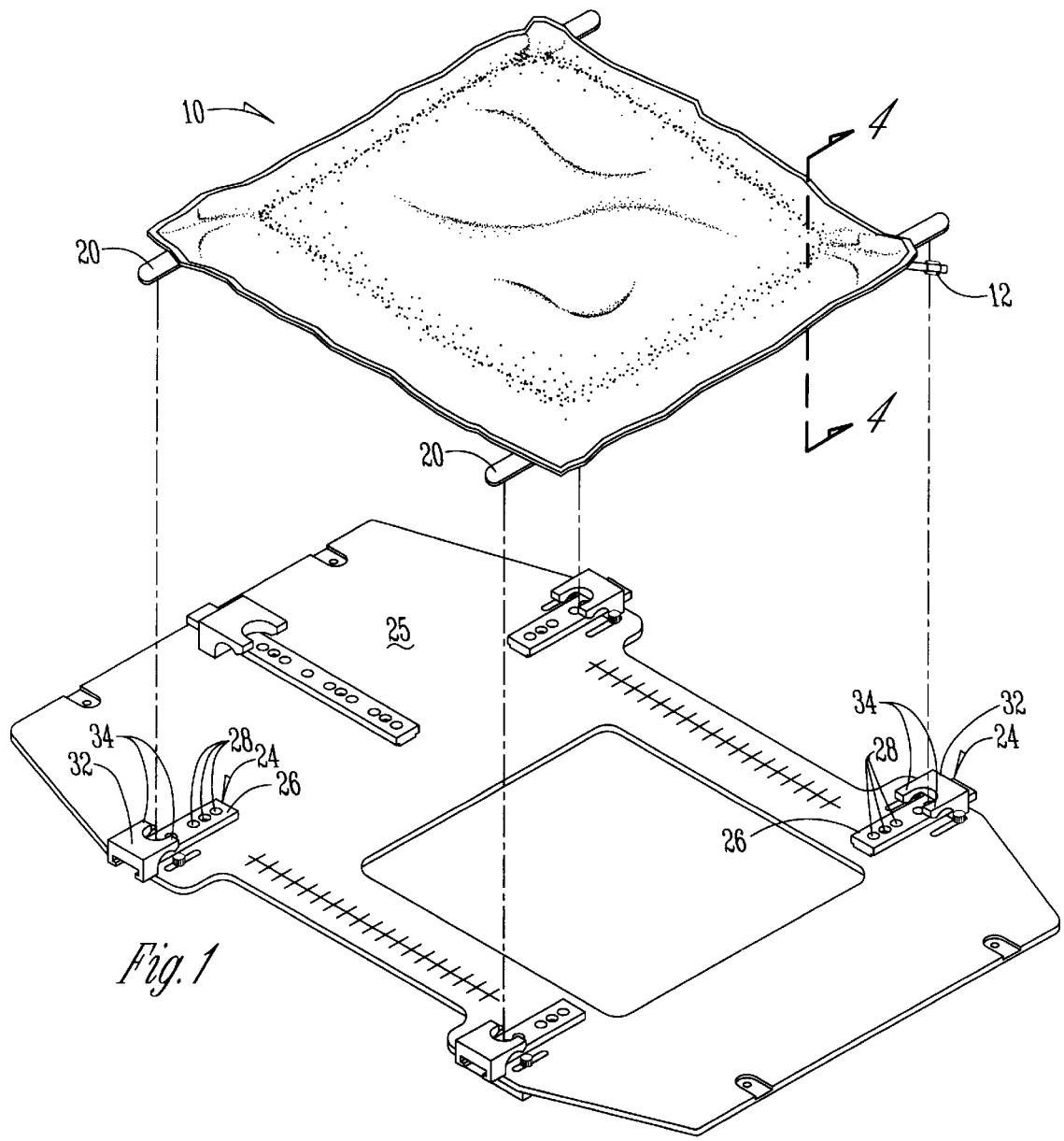
FIGS. 1 is a perspective view of a one embodiment of the vacuum cushion of the present invention positioned above a baseplate.
Figure 2:
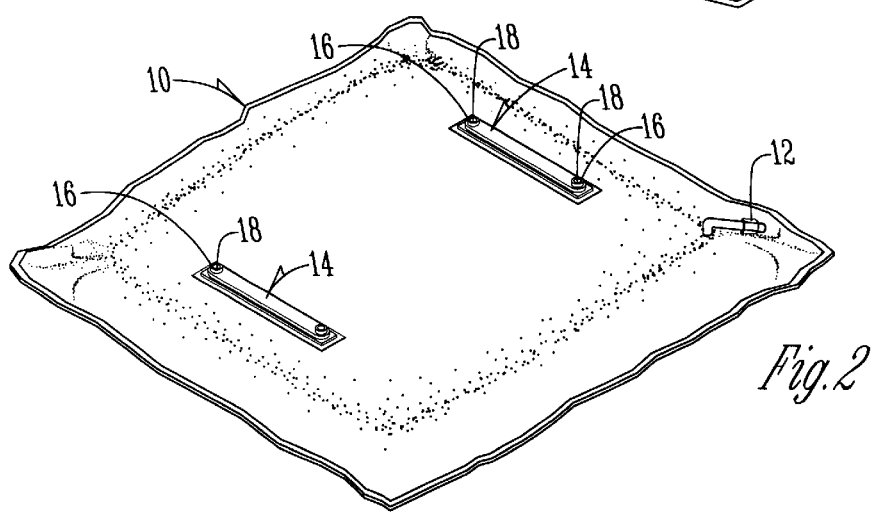
FIG. 2 is a perspective view of the bottom side of the cushion without the elongated indexing bars.

With reference to the drawings, the numeral 10 generally designates a moldable vacuum cushion for positioning a patient during radiation therapy treatments, diagnostic imaging and other medical procedures. The outer casing 11 of the cushion 10 preferably is made from a flexible, non-porous material, such as a urethane film or nylon reinforced urethane. The nylon reinforced polyurethane is more durable and has a longer life than flexible urethane film used in conventional vacuum cushions. The cushion is partially filled with a yieldable substance, such as polystyrene spheres 0.060 inch in diameter. A valve 12 is provided for inflating and deflating the cushion 10.

Figure 3:
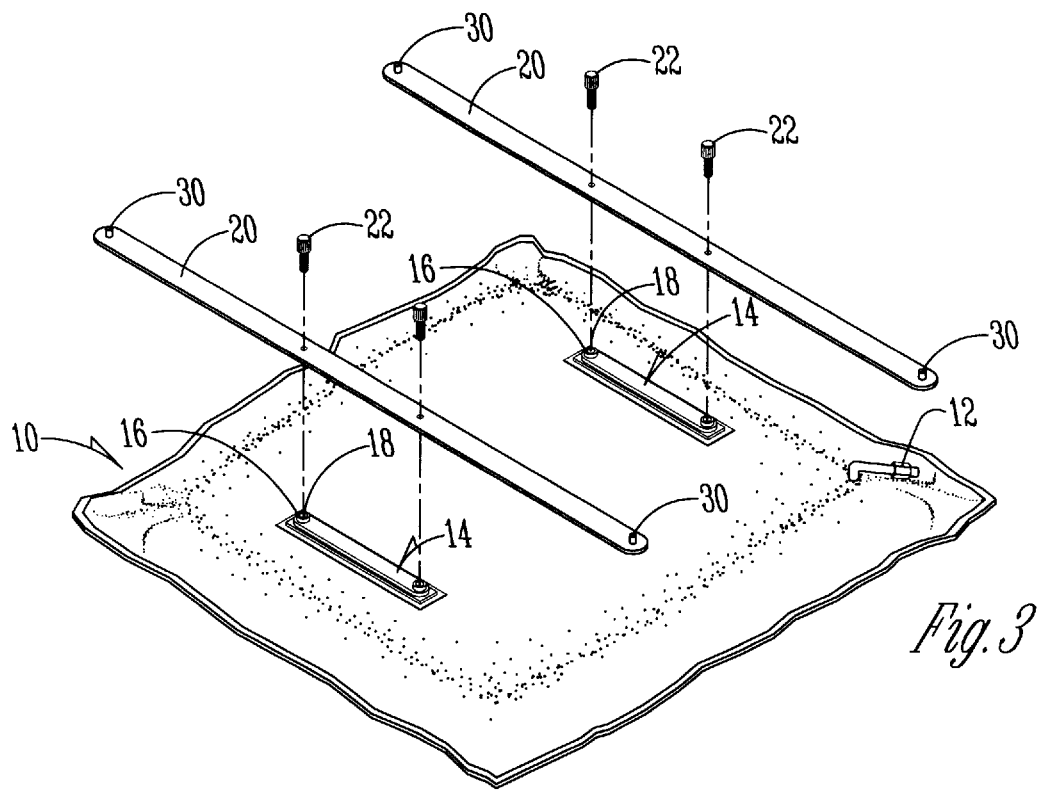
FIG. 3 is an exploded perspective view from the bottom side of the indexing bars and cushion.
Figure 4:
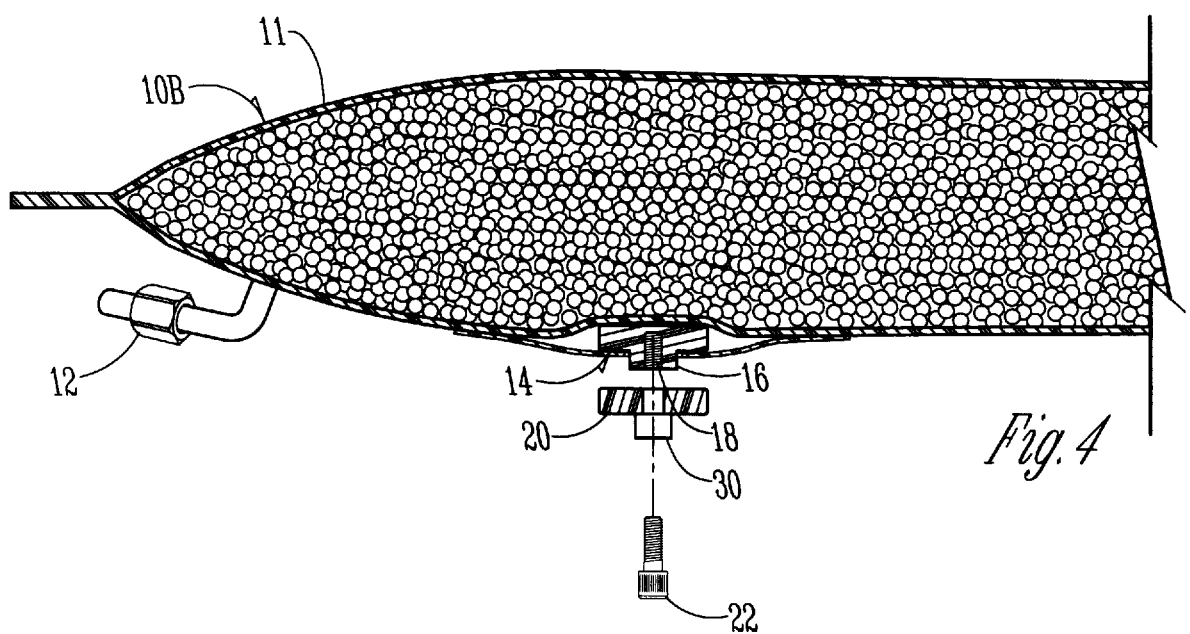
FIG. 4 is a sectional view taken along lines 4—4 of FIG. 1.

As best seen in FIGS. 3 and 4, sandwiched between two layers of the casing material 11 is one or more frame members 14. The opposite ends of each frame member 14 includes studs 16 having a threaded hole 18 therein. An elongated indexing bar 20 is adapted to be secured to each frame member 14 by conventional screws or threaded fasteners 22. The ends of the bar 20 may extend beyond the edges of the cushion 10, as shown in FIGS. 1 and 3. Alternatively, the length of the indexing bar may be less than the dimensions of the cushion, with the edge of the cushion being movable to allow access to the ends of the shorter indexing bar.

As best seen in FIG. 1, the indexing bars 20 are adapted to be indexed and locked with slide lock devices 24. The slide locks 24 are provided on the baseplate 25 for securing the indexing bars 20, and thereby the cushion 10, to the baseplate. The slide locks 24 are described in detail in Applicant's co-pending application Ser. No. 08/851,371, filed on May 5, 1997, which is incorporated herein by reference. Generally, each slide lock device 24 includes a T-shaped rail 26 secured to the baseplate 25 or treatment table. The T-shaped rail 26 includes a plurality of indexing holes 28 to selectively receive an indexing pin 30 on the bottom of the indexing bar 20. A C-shaped tab 32 slides along the T-shaped rail 26 and has a pair of fingers 34 which overlap and engage the end of the indexing bar 20, thereby locking the bar 20, and thus the cushion 10 into a selected indexed position on the baseplate 25 or treatment table.

Figure 5:
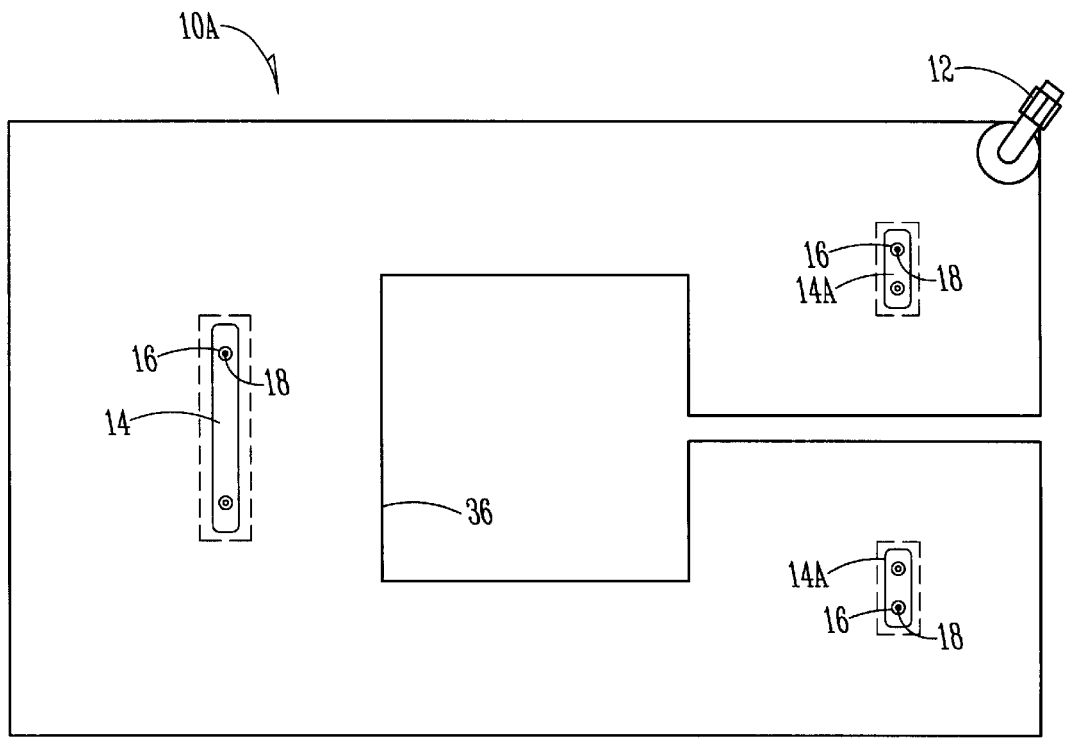
FIG. 5 is a plan view of an alternatively shaped vacuum cushion in accordance with the present invention.

FIG. 5 shows an alternatively-shaped vacuum 10A having a cut-out or window 36 for specific radiation therapy applications. The vacuum cushion 10A includes frame members 14 and 14A, similar to that described above with respect to cushion 10. Frame members 14A include studs 16 and threaded holes 18 for attaching an indexing bar (not shown).

Figure 6:
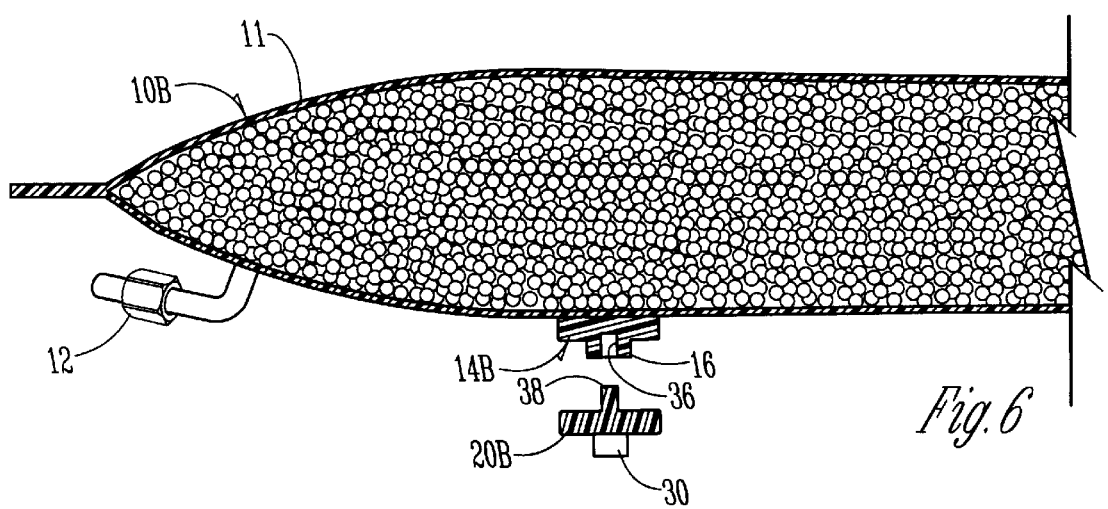
FIG. 6 is a sectional view similar to FIG. 4 showing a second embodiment of the invention.

FIG. 6 shows yet another embodiment of the invention, wherein a vacuum cushion 10B includes a frame member 14B which is connected to the outside of the cushion 10B with adhesive or other conventional means. Thus, the frame member 14B is not sandwiched between two layers of the casing material, as in the first embodiment shown in FIGS. 1–4. The frame member 14B includes a stud 16 and a recess 36. The indexing bar 20B has a peg 38 adapted to be snap fit within the recess 36, thereby quickly and easily connecting the bar 20B to the frame member 14B. The bar 20B also includes an indexing pin 30 for selectively mounting the indexing bar to a slide lock device, as described above.

Figure 7:
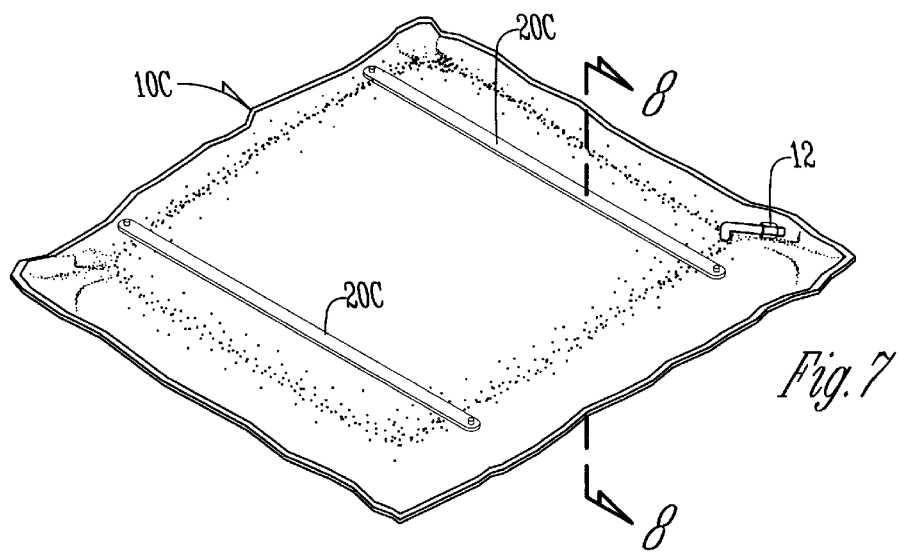
FIG. 7 is a perspective view of a third embodiment of the invention.
Figure 8:
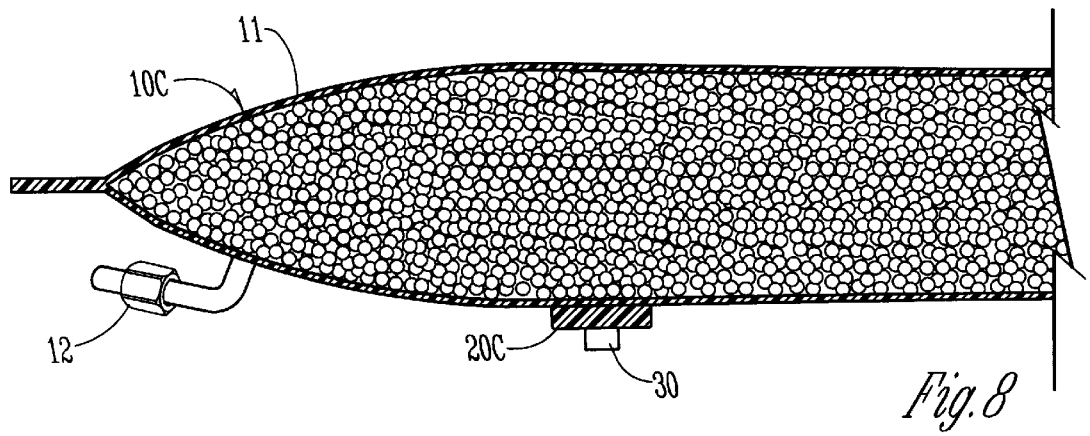
FIG. 8 is a sectional view taken along lines 8—8 of FIG. 7.

FIGS. 7 and 8 show a fourth embodiment of the present invention wherein the indexing bar 20C is directly mounted upon the vacuum cushion 10C without the use of a frame member. The indexing bar 20C includes an indexing pin 30 for receipt in a slide lock, as described above.

Figure 9:
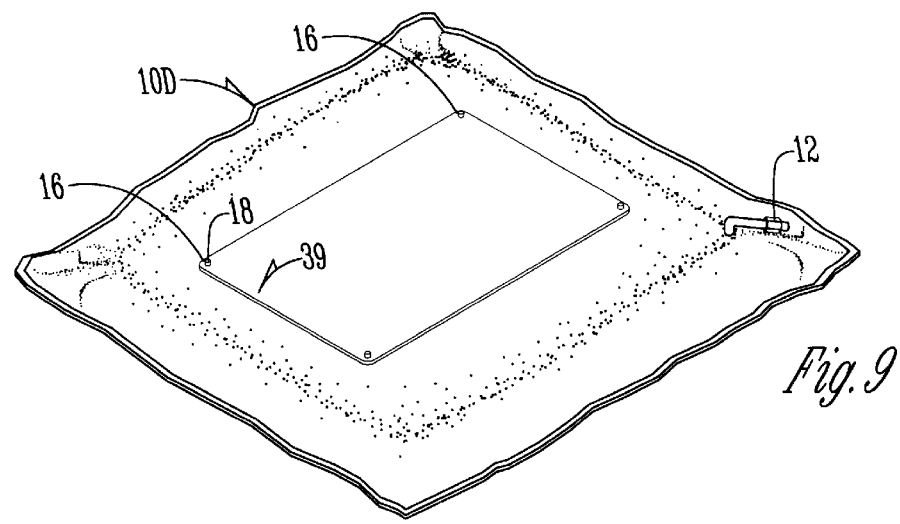
FIG. 9 is a perspective view of a fourth embodiment of the invention.

FIG. 9 shows still another embodiment wherein the frame member 39 is in the form of an enlarged plate member mounted on the cushion 10D using adhesive or other conventional mounting means. The plate 39 includes studs 16 with a threaded aperture 18 or a recess for mounting an indexing bar, such as bar 20 or 20B.

Figure 10:
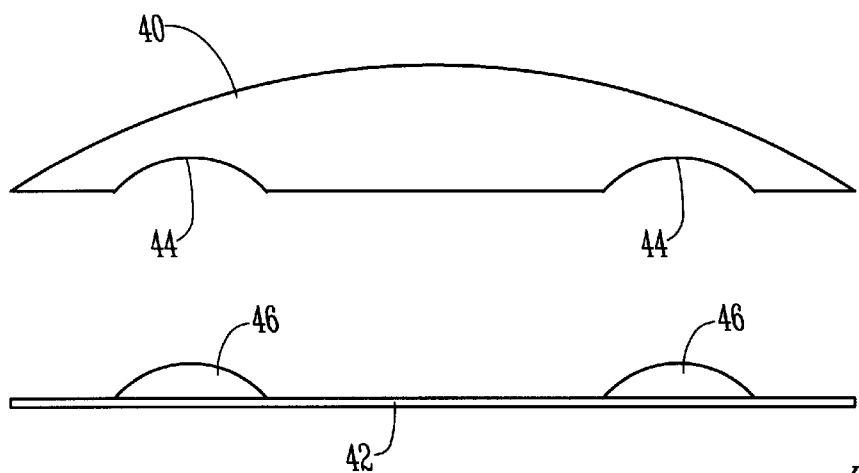
FIG. 10 is an exploded side view of a prior art vacuum cushion and baseplate.

A prior art patient positioning cushion 40 is shown in FIG. 10. When the cushion 40 is molded on the baseplate 42 by pulling a vacuum through the cushion valve, detents 44 are formed on the bottom of the cushion 40 and corresponding to the protrusions 46 on the baseplate. This prior art cushion 40 does not provide the critical tolerances necessary for high precision radiation therapy treatments.

In comparison, the interconnected cushion with the frame member and/or indexing bar of the present invention allows precise and repeatable indexing of the cushion to the baseplate 25 or to a treatment table in a quick, easy, accurate, and repeatable manner.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A vacuum cushion for positioning a patient on a support surface for radiation therapy treatment, comprising:

a moldable cushion with a valve adapted to be connected to a vacuum source;

a bar secured to the cushion and having opposite ends for attachment to the support surface;

the bar having opposite ends with indexing pins for indexing the cushion to the support surface.

2. The vacuum cushion of claim 1 further comprising a frame member fixed on the cushion, the bar being releasably securable to the frame member.

3. The vacuum cushion of claim 2 wherein the frame member is sandwiched between two layers of casing material.

4. The vacuum cushion of claim 2 further comprising threaded fasteners for releasably connecting the bar to the frame member.

5. The vacuum cushion of claim 2 wherein the frame member and bar have mating members for snap fitting the frame member and bar together.

6. The vacuum cushion of claim 1 wherein the cushion includes an outer casing constructed of a flexible, non-porous material, the casing being partially filled with a yieldable substance.

7. A vacuum cushion for positioning a patient for a medical procedure, comprising:

a cushion having an outer flexible casing filled with a yieldable substance such that the cushion is moldable to conform to an anatomical area of the patient;

a frame member fixed on the outer casing;

a bar connected to the frame member and being adapted to be secured to a base plate or table, thereby holding the cushion in position for the medical procedure.

8. The vacuum cushion of claim 7 wherein the cushion has a perimeter edge and the bar extends beyond the perimeter edge of the cushion.

9. The vacuum cushion of claim 7 wherein the bar includes indexing pins adapted to be selectively positioned in indexing holes in the base plate or table.

10. The vacuum cushion of claim 7 wherein the bar is releasably connected to the frame member.

11. The vacuum cushion of claim 7 wherein the bar is threadably connected to the frame member.

12. The vacuum cushion of claim 7 wherein the bar is snap fit to the frame member.

13. The vacuum cushion of claim 7 wherein the frame member is fixed between two layers of casing material.

14. The vacuum cushion of claim 7 wherein the casing is made of a flexible, non-porous material.

15. The vacuum cushion of claim 7 wherein the yieldable substance is spherical beads.

16. A method of indexing a patient cushion to a support surface for repeated medical treatments of the patient, comprising:

attaching an indexing bar directly to the cushion; and securing the bar to the support surface in a selected indexed position; and selectively positioning indexing pins on the bar into indexing holes in the support surface.

17. The method of claim 16 further comprising releasably mounting the indexing bar to the cushion.

18. The method of claim 16 further comprising releasably mounting the indexing bar to a frame member on the cushion.

19. A vacuum cushion for positioning a patient on a support surface for radiation therapy treatment, comprising:

a moldable cushion with a valve adapted to be connected to a vacuum source;

a bar secured to the cushion and having opposite ends for attachment to the support surface; and a frame member fixed on the cushion;

the bar being releasably securable to the frame member;

the frame member and the bar having mating members for snap fitting the frame member and the bar together.

* * * * *